United States Patent
Kim et al.

(10) Patent No.: US 10,575,965 B2
(45) Date of Patent: Mar. 3, 2020

(54) SPINAL IMPLANT WITH UNIT STRUCTURE PRINTED USING 3D PRINTER

(71) Applicant: Mantiz Logitech Co., Ltd., Daegu (KR)

(72) Inventors: Eui-Jun Kim, Daegu (KR); Il-Hwan Lee, Busan (KR); Jeong yoon Park, Seongnam-si (KR); Hong Won Yoon, Busan (KR)

(73) Assignee: MANTIZ LOGITECH CO., LTD., Daegu (KR)

( * ) Notice: Subject to any disclaimer, the term of this patent is extended or adjusted under 35 U.S.C. 154(b) by 0 days.

(21) Appl. No.: 15/983,707

(22) Filed: May 18, 2018

(65) Prior Publication Data

US 2019/0000636 A1    Jan. 3, 2019

(30) Foreign Application Priority Data

Jun. 29, 2017   (KR) .................. 10-2017-0082465

(51) Int. Cl.
*A61F 2/44* (2006.01)
*B33Y 80/00* (2015.01)
*A61F 2/30* (2006.01)

(52) U.S. Cl.
CPC ............ *A61F 2/447* (2013.01); *A61F 2/4455* (2013.01); *B33Y 80/00* (2014.12); *A61F 2002/302* (2013.01); *A61F 2002/3092* (2013.01); *A61F 2002/30092* (2013.01); *A61F 2002/30115* (2013.01); *A61F 2002/30179* (2013.01); *A61F 2002/30331* (2013.01); *A61F 2002/30563* (2013.01); *A61F 2002/30985* (2013.01); *A61F 2002/4415* (2013.01); *A61F 2002/4495* (2013.01); *A61F 2310/00023* (2013.01)

(58) Field of Classification Search
CPC .............. A61F 2/447; A61F 2002/4475; A61F 2002/4495; A61F 2/4465; A61F 2/446; A61F 2/4455

See application file for complete search history.

(56) References Cited

U.S. PATENT DOCUMENTS

| 6,206,924 B1* | 3/2001 | Timm ................. A61F 2/28 623/17.11 |
| 2005/0112397 A1* | 5/2005 | Rolfe ............... A61B 17/8605 428/593 |
| 2011/0313532 A1* | 12/2011 | Hunt ................ A61F 2/30767 623/18.11 |

(Continued)

FOREIGN PATENT DOCUMENTS

| KR | 10-2002-0068038 A | 8/2002 |
| KR | 10-2013-0037243 A | 4/2013 |

(Continued)

*Primary Examiner* — Julianna N Harvey
(74) *Attorney, Agent, or Firm* — Novick, Kim & Lee, PLLC; Jae Youn Kim

(57) ABSTRACT

Provided is a spinal implant having a unit structure printed by using a 3D printer, which is inserted between a vertebra and an adjacent vertebra and in which unit bodies constituted by at least one or more circular rings are repeated with a certain pattern. The spinal implant may implement elastic force like the existing vertebrae while bone fusion is performed as well as a state in which the bone fusion is completed after a procedure to obtain superior procedure results.

8 Claims, 11 Drawing Sheets

(56) References Cited

U.S. PATENT DOCUMENTS

| | | | | |
|---|---|---|---|---|
| 2013/0116793 | A1* | 5/2013 | Kloss | A61F 2/442 |
| | | | | 623/17.16 |
| 2013/0325129 | A1* | 12/2013 | Huang | A61F 2/44 |
| | | | | 623/17.16 |
| 2016/0022431 | A1* | 1/2016 | Wickham | A61F 2/447 |
| | | | | 623/17.16 |
| 2016/0184103 | A1* | 6/2016 | Fonte | A61L 27/306 |
| | | | | 623/23.5 |
| 2017/0156878 | A1* | 6/2017 | Tsai | A61F 2/442 |
| 2017/0156880 | A1* | 6/2017 | Halverson | A61F 2/0077 |
| 2017/0333205 | A1* | 11/2017 | Joly | A61F 2/4465 |
| 2018/0110624 | A1* | 4/2018 | Arnone | A61F 2/30771 |
| 2018/0256336 | A1* | 9/2018 | Mueller | A61F 2/30 |

FOREIGN PATENT DOCUMENTS

| | | |
|---|---|---|
| KR | 10-2015-0130528 A | 11/2015 |
| KR | 10-2016-0128236 A | 11/2016 |

* cited by examiner

SPINAL IMPLANT WITH UNIT STRUCTURE PRINTED USING 3D PRINTER

CROSS-REFERENCE TO RELATED APPLICATIONS

This U.S. non-provisional patent application claims priority under 35 U.S.C. § 119 of Korean Patent Application No. 10-2017-0082465, filed on Jun. 29, 2017, the entire contents of which are hereby incorporated by reference.

BACKGROUND

The present invention relates to a spinal implant having a unit structure that is printed by using a 3D printer, and more particularly, to a spinal implant having a unit structure printed by using a 3D printer, which is capable of implementing elastic force like the existing vertebrae while bone fusion is performed as well as a state in which the bone fusion is completed after a procedure to obtain superior procedure results.

A disc existing between vertebrae functions as a joint and plays very important roles for minimizing an impact applied to a spine while vertebral pulp accommodated inside the disc changes in position and shape according to the movement of the vertebrae.

The vertebral pulp is mostly moisture (water). When we get older, an amount of moisture gradually decreases, and thus, a buffer function of a disc is lost.

As a result, when an excessive pressure is applied to the fibers, backache may occur. Here, if the excessive pressure is continuously applied, the fibers may be seriously stretched or ruptured to push nerve roots placed at a rear side thereof, thereby causing pains of pelvis, legs, and the like.

Thereafter, a distance between the vertebrae gradually decreases, or the vertebrae are collapsed to cause various kinds of side effects such as vertebral deformation.

There is a method, in which an intervertebral fusion cage, so-called, a cage is inserted between two adjacent vertebrae after a disc between the damaged vertebrae is removed, as a method for treating diseases involved due to the disc.

That is, the cage recovers the distance between the vertebrae to its original distance between the two adjacent vertebrae, which corresponds to an original height of the disc, thereby recovering the vertebral function.

However, the general intervertebral fusion cage has a solid structure made of a metal material such as titanium or a titanium alloy. Thus, there is a limitation that facing surfaces of the vertebrae adjacent to each other subside by top and bottom surfaces of the age after the intervertebral fusion cage is inserted between the vertebrae to complete the procedure.

As an invention derived in view of the above-mentioned points, an intervertebral fusion cage utilizing various kinds of 3D printing techniques as illustrated in FIG. 11, which include "a method for producing a porous metal implant and a porous metal implant manufactured thereby (hereinafter, referred to as a prior art)", which is disclosed in Korean Patent Publication No. 10-2016-0128236, has been developed.

Each of the intervertebral fusion cages manufactured by the prior art and the existing 3D printing manufacturing method illustrated in FIG. 11 has a mesh structure having a linear lattice shape on the whole so as to improve the bone fusion.

However, although all the intervertebral fusion cages manufactured by the existing 3D printing manufacturing method including the prior art has been done to some extent, there is almost no generation of elastic force for realizing a buffering effect with respect to a pressure and an impact due to a weight and a posture change of a person to be surgically operated (hereinafter, referred to as a subject).

Thus, the existing 3D printing manufacturing method, in which there is no elastic force in the process of performing the bone fusion after the procedure, i.e., until the bone fusion is completely performed, does not prevent the subsidence phenomenon that occurs on the facing surfaces of the vertebrae adjacent to each other.

In addition, after the bone fusion is completed, natural elastic force that absorbs an impact of the human body like the existing vertebrae is not provided.

SUMMARY

The present invention provides a spinal implant having a unit structure printed by using a 3D printer, which is capable of implementing elastic force like the existing vertebrae while bone fusion is performed as well as a state in which the bone fusion is completed after a procedure to obtain superior procedure results.

The present invention also provides a spinal implant having a unit structure printed by using a 3D printer, which is capable of preventing a subsidence phenomenon that occurs on the facing surfaces of vertebrae adjacent to each other from occurring by a structure that provides sufficient elastic force unlike the existing spinal implant in a process of performing bone fusion after a procedure, i.e., even before the bone fusion is completely performed.

An embodiment of the present invention provides a spinal implant having a unit structure printed by using a 3D printer, the spinal implant including a bone fusion unit printed by using the 3D printer, which is inserted between a vertebra and an adjacent vertebra and in which unit bodies constituted by at least one or more circular rings are repeated with a certain pattern.

The certain pattern may include: a first layer in which the plurality of circular rings are disposed on the same plane to provide a row or column; and a second layer in which the plurality of circular rings having a row or column, which is perpendicular to that of the first layer, are disposed, wherein, in the certain pattern, patterns on which the first layer and the second layer coming into contact with each other may be repeated upward, downward, left, right, forward, and backward, and edges of the plurality of circular rings may come into contact with each other.

The certain pattern may include: a third layer in which the plurality of circular rings are disposed on the same plane to provide a row or column; and a fourth layer in which the plurality of circular rings having a row or column, which is perpendicular to that of the third layer, are disposed, wherein the third layer may be disposed to be inclined at a predetermined angle with respect to a separate virtual plane, in the certain pattern, patterns on which the third layer and the fourth layer coming into contact with each other may be repeated upward, downward, left, right, forward, and backward, and edges of the plurality of circular rings may come into contact with each other.

The certain pattern may include a first unit solid in which the at least two or more circular rings cross each other to share a first virtual line that passes through diameters of the circular rings and thereby to provide two intersections, wherein, in the certain pattern, the plurality of first unit solids may be repeated upward, downward, left, right, forward, and backward, and the two intersections may respectively face a bottom surface of the vertebra and a top surface of a vertebra adjacent to the vertebra.

The certain pattern may include a second unit solid in which the at least two or more circular rings cross each other to share a second virtual line that passes through diameters of the circular rings and thereby to provide two intersections, wherein, in the certain pattern, the plurality of second unit solids may be repeated upward, downward, left, right, forward, and backward, and the second virtual line passing through the two intersections may pass through a space between the vertebra and the adjacent vertebra.

The spinal implant may further include a main frame which is inserted between the vertebra (hereinafter, referred to as a first vertebra) and the adjacent vertebra (hereinafter, referred to as a second vertebra), provides an inner space for accommodating the bone fusion unit, and is printed together with the bone fusion unit by using the 3D printer, wherein top and bottom surfaces, left and right surfaces, and a rear surface of the bone fusion unit may be exposed to the outside.

The main frame may include: a pair of upper bars disposed in parallel to each other to face a bottom surface of the first vertebra; a pair of lower bars disposed in parallel to each other to face a top surface of the first vertebra; an upper insertion bar extending to be inclined downward from a front end of each of the pair of upper bars; and a lower insertion bar extending to be inclined upward from a front end of each of the pair of lower bars, wherein the bone fusion unit may be disposed in an inner space that is defined by the pair of upper bars, the pair of lower bars, the upper insertion bars, and the lower insertion bars.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings:

FIGS. 5A and 5B are views when viewed in direction of arrows Va and Vb of FIG. 2, wherein FIG. 5A is a conceptual front view, and FIG. 5B is a conceptual rear view.

FIGS. 9A and 9B are views when viewed in direction of arrows IXa and DO of FIG. 6, wherein FIG. 9A is a conceptual front view, and FIG. 9B is a conceptual rear view.

DETAILED DESCRIPTION

Figure 1A:
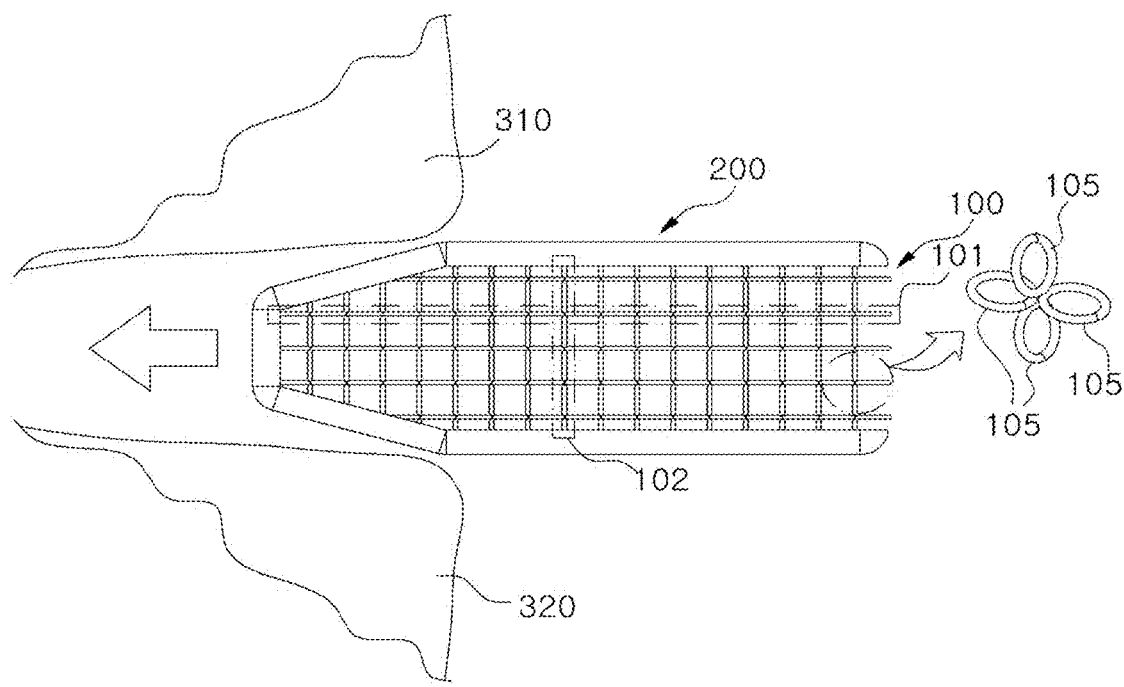
FIGS. 1A and 1B are conceptual side views of a spinal implant having a unit structure that is printed by a 3D printer according to an embodiment of the present invention.

Advantages and features of the present disclosure, and implementation methods thereof will be clarified through following embodiments described with reference to the accompanying drawings.

The present invention may, however, be embodied in different forms and should not be construed as limited to the embodiments set forth herein.

In this specification, these embodiments are provided so that this disclosure will be thorough and complete, and will fully convey the scope of the present invention to those skilled in the art.

Also, the present invention is only defined by scopes of claims.

Accordingly, in some embodiments, well-known components, well-known device operations, and well-known techniques will not be described in detail to avoid ambiguous interpretation of the present invention.

Also, like reference numerals refer to like elements throughout. In the following description, the technical terms are used (mentioned) only for explaining a specific exemplary embodiment while not limiting the present disclosure.

The terms of a singular form may include plural forms unless referred to the contrary. The meaning of "include," "comprise," "including," or "comprising," specifies a component and an operation but does not exclude other components and operations.

Unless terms used in the present invention are defined differently, all terms (including technical and scientific terms) used in this specification have the same meaning as generally understood by those skilled in the art.

Also, unless defined apparently in the description, the terms as defined in a commonly used dictionary are not ideally or excessively construed as having formal meaning.

Hereinafter, preferred embodiments of the present invention will be described in more detail with reference to the accompanying drawings.

Figure 1B:
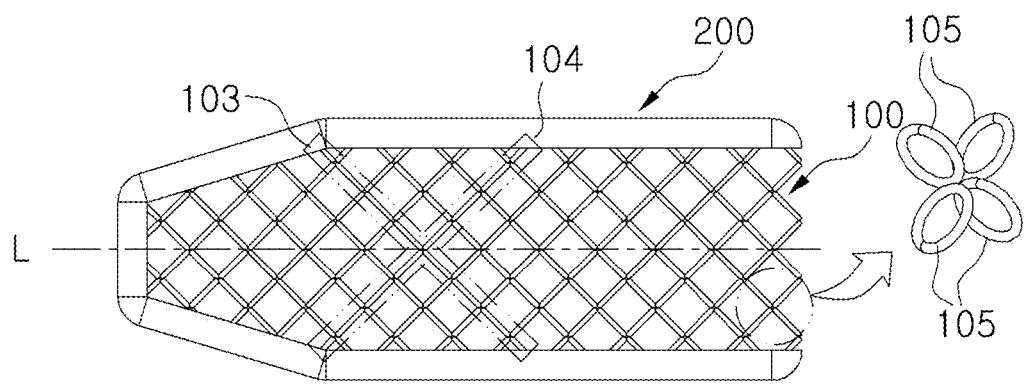

First, FIGS. 1A and 1B are conceptual side views of a spinal implant having a unit structure that is printed by a 3D printer according to an embodiment of the present invention.

Figure 2:
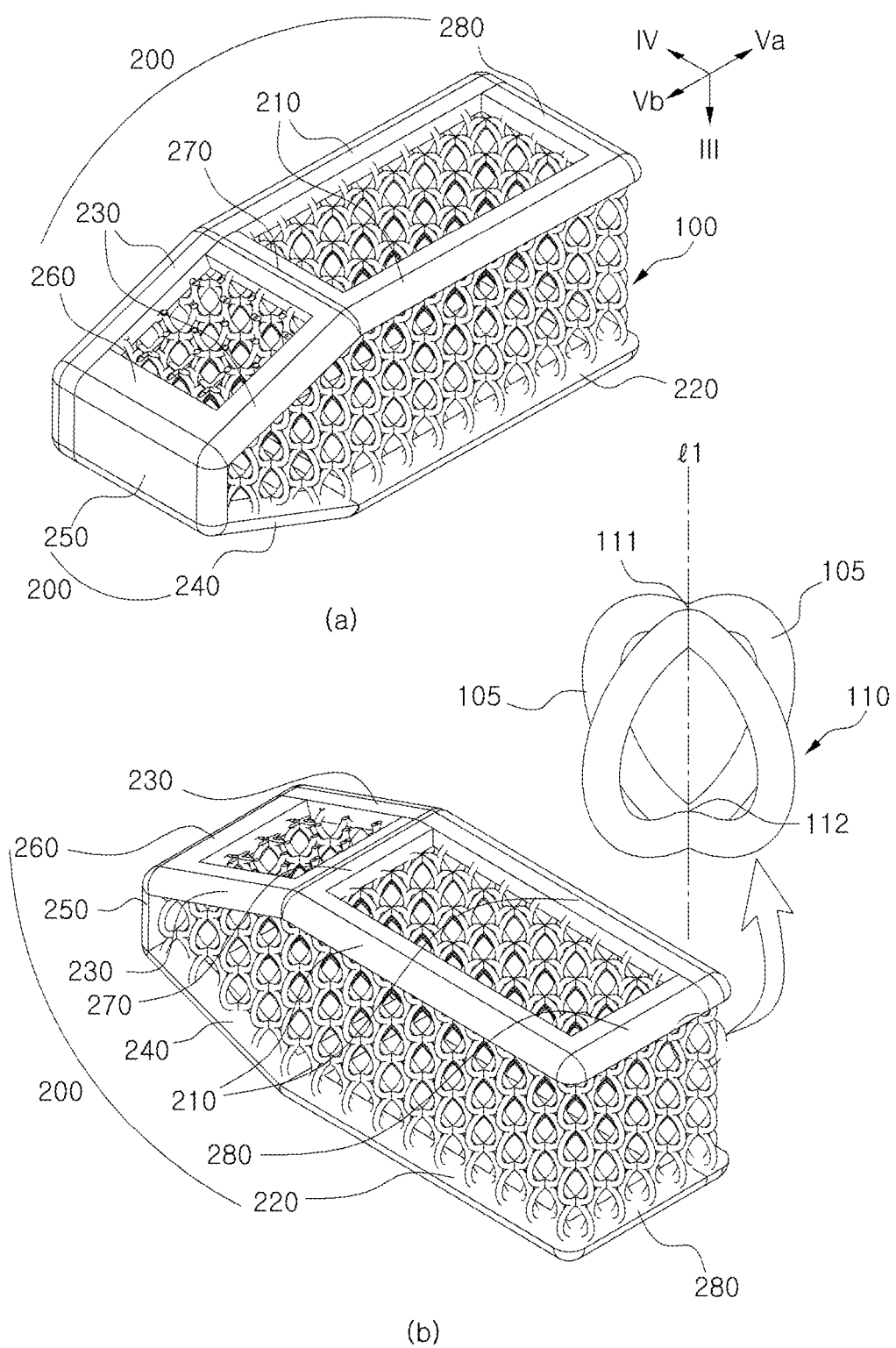
FIG. 2 is a perspective view illustrating an outer appearance of a spinal implant having a unit structure that is printed by a 3D printer according to another embodiment of the present invention.
Figure 3:
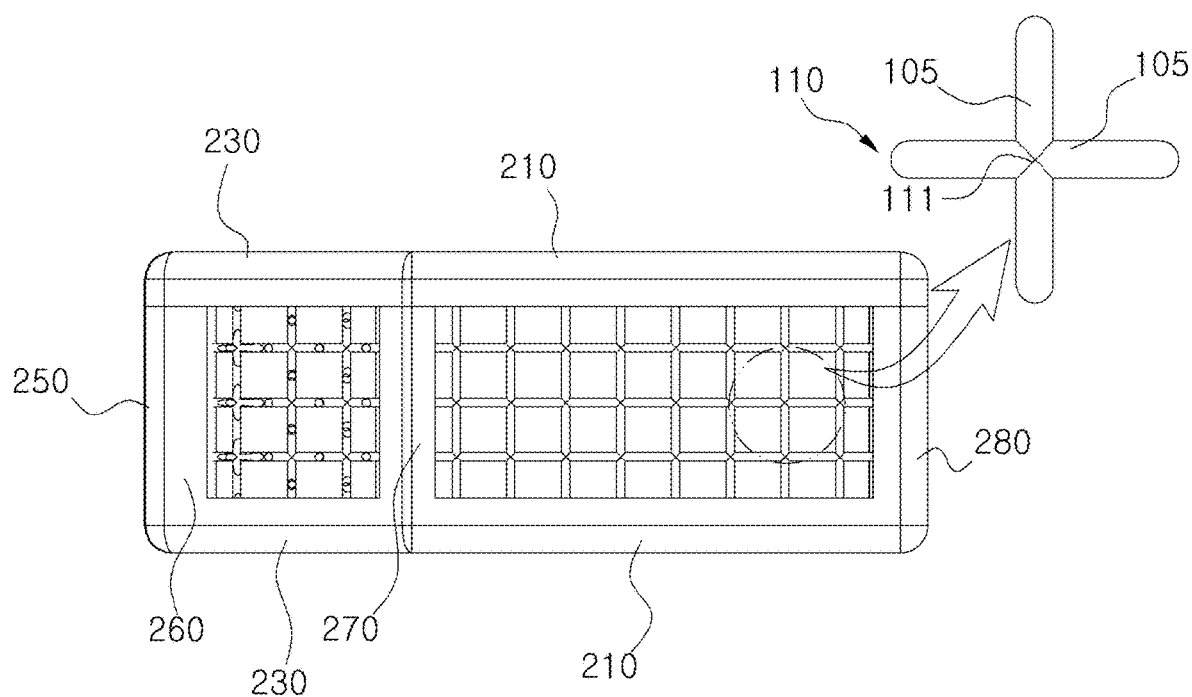
FIG. 3 is a conceptual plan view when viewed in a direction of an arrow III of FIG. 2.
Figure 4:
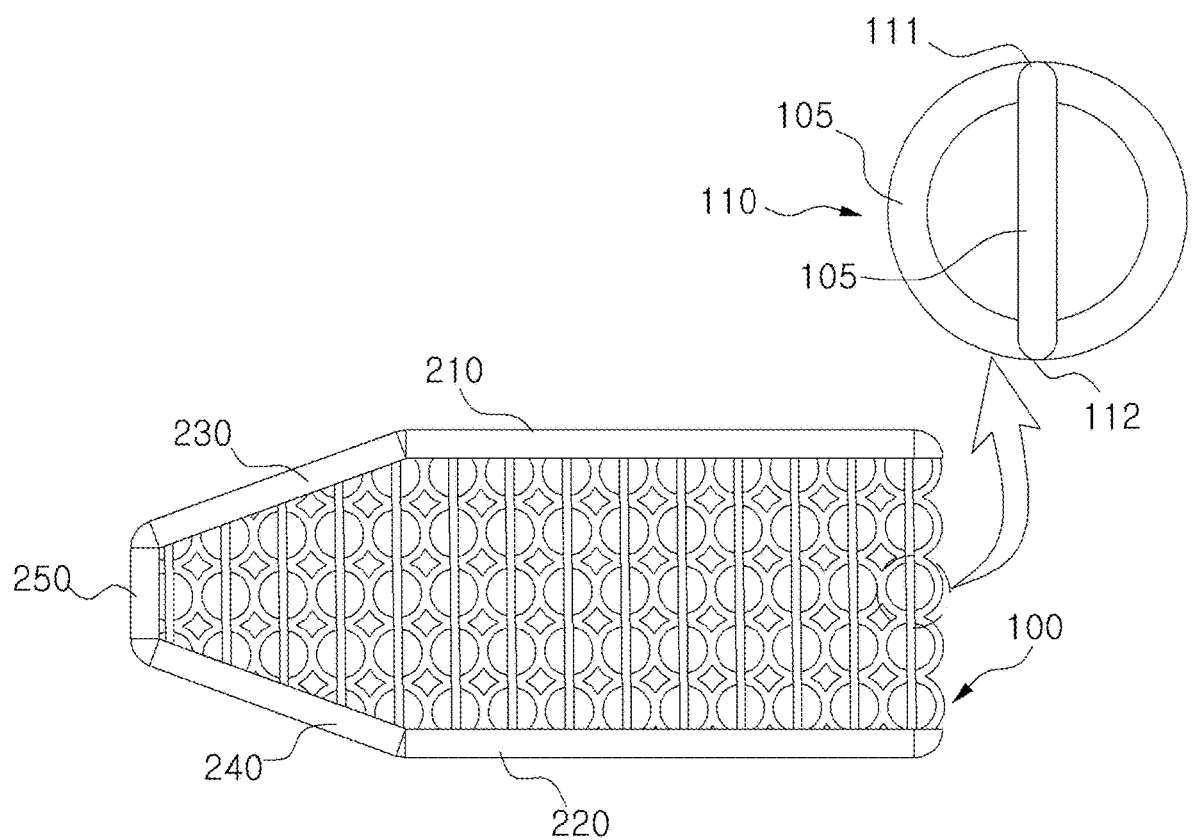
FIG. 4 is a conceptual side view when viewed in a direction of an arrow IV of FIG. 2.
Figure 5A:
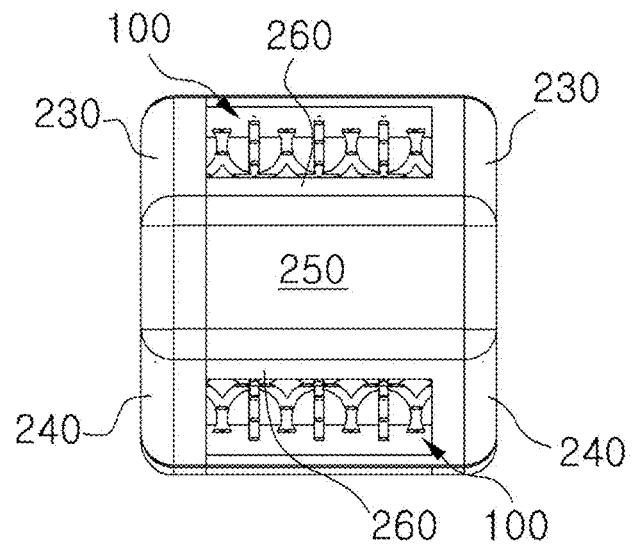
Figure 5B:
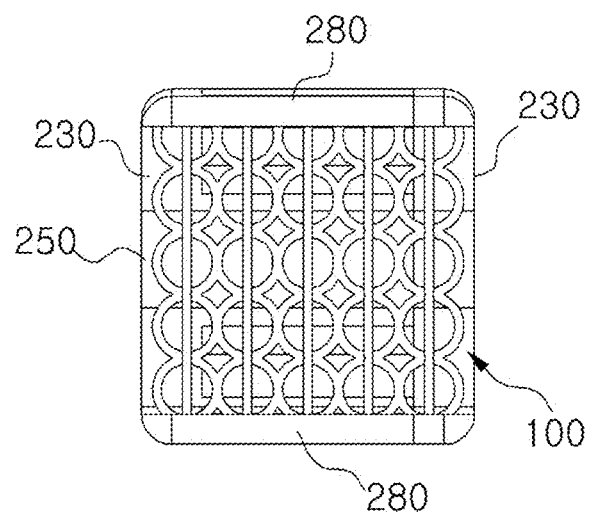

Also, FIG. 2 is a perspective view illustrating an outer appearance of a spinal implant having a unit structure that is printed by a 3D printer according to another embodiment of the present invention, FIG. 3 is a conceptual plan view when viewed in a direction of an arrow III of FIG. 2, FIG. 4 is a conceptual side view when viewed in a direction of an arrow IV of FIG. 2, and FIGS. 5A and 5B are views when viewed in direction of arrows Va and Vb of FIG. 2, wherein FIG. 5A is a conceptual front view, and FIG. 5B is a conceptual rear view.

Figure 6:
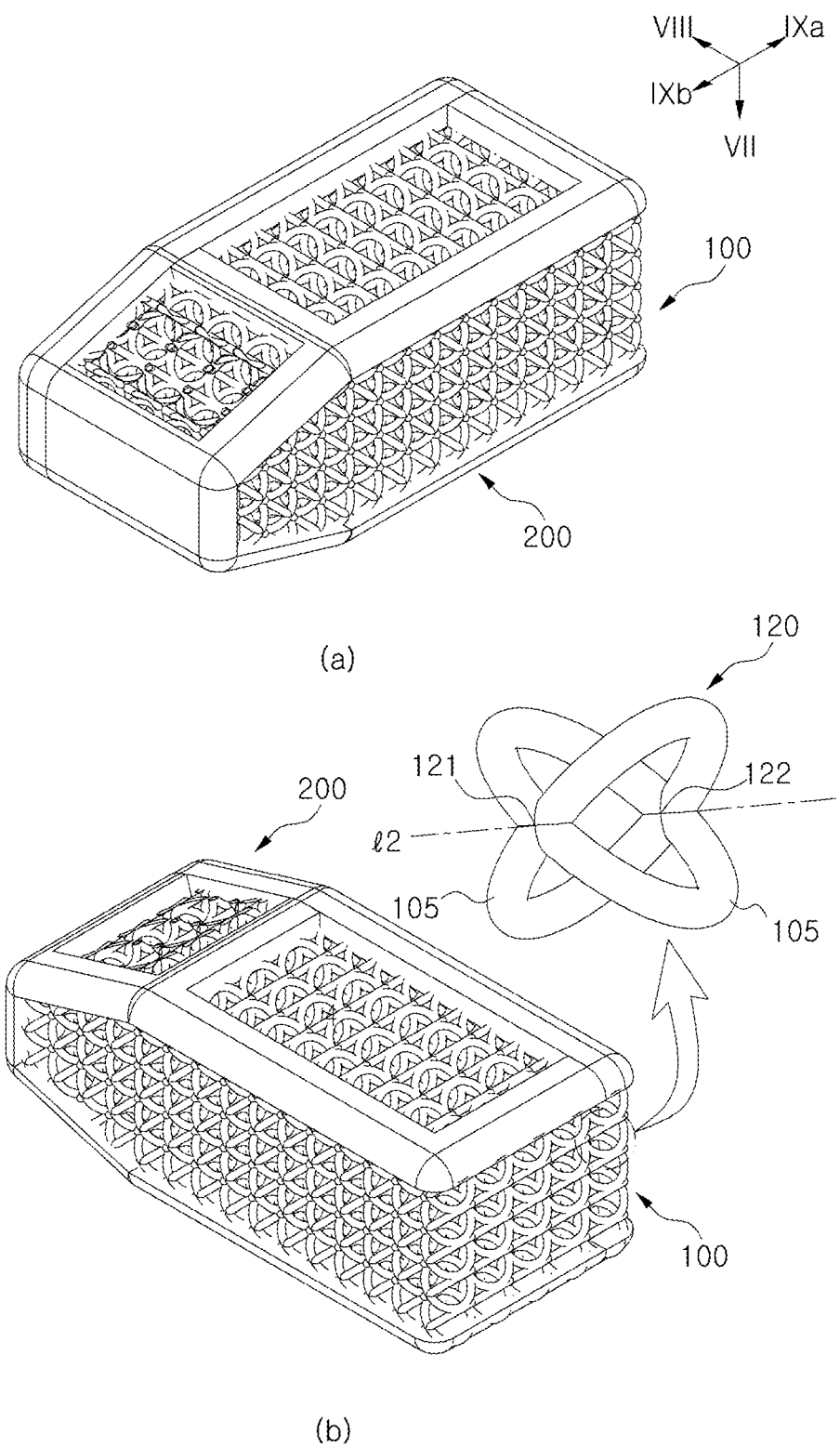
FIG. 6 is a perspective view illustrating an outer appearance of a spinal implant having a unit structure that is printed by a 3D printer according to further another embodiment of the present invention.
Figure 7:
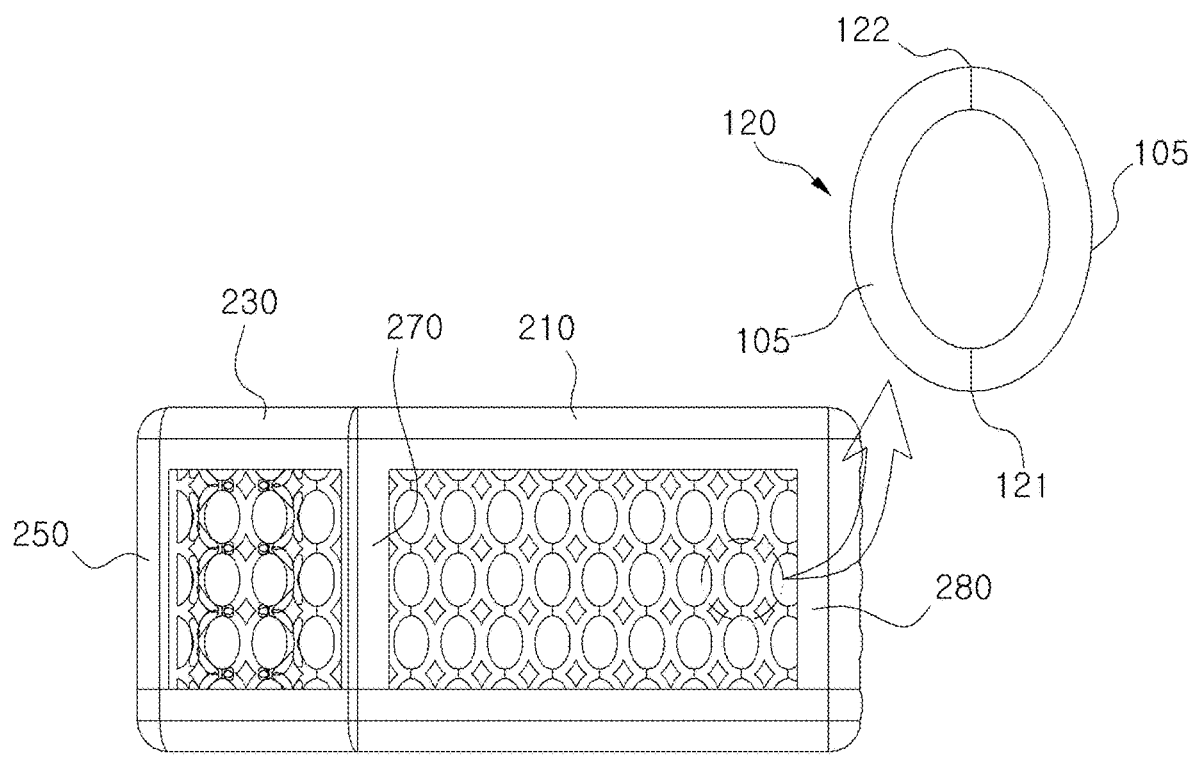
FIG. 7 is a conceptual plan view when viewed in a direction of an arrow VII of FIG. 6.
Figure 8:
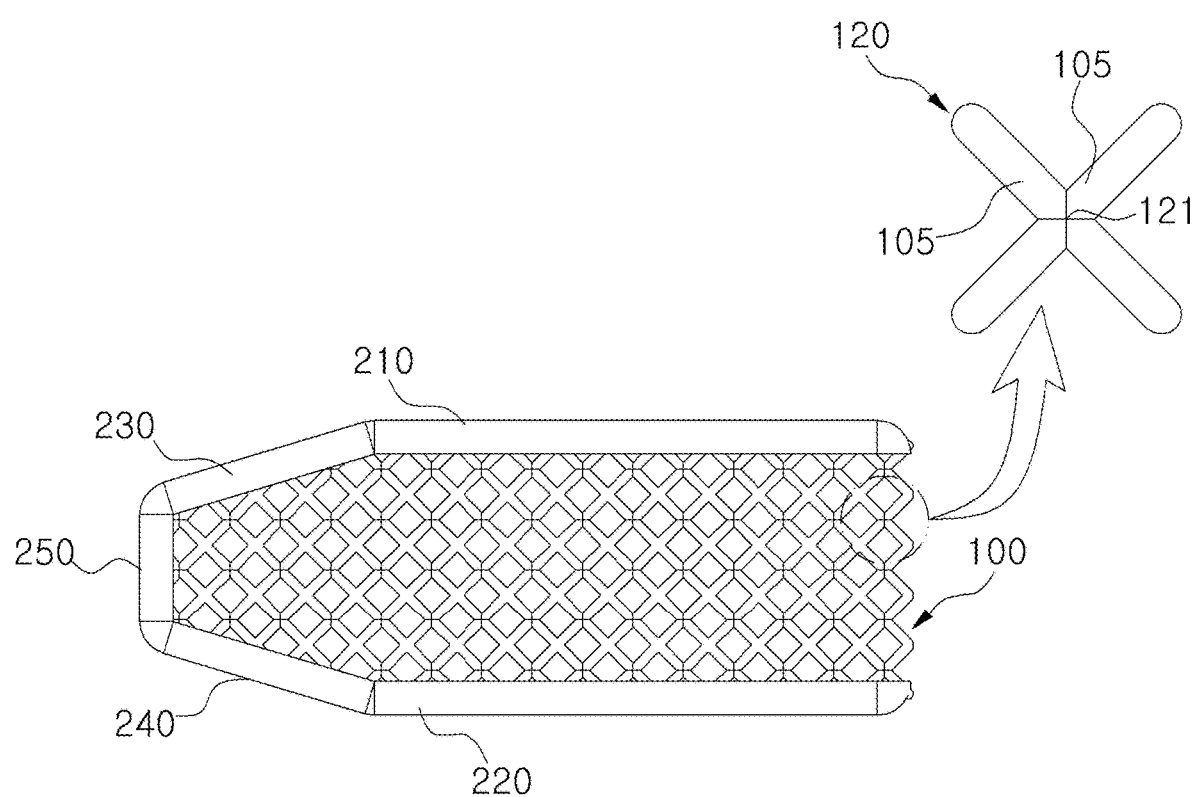
FIG. 8 is a conceptual side view when viewed in a direction of an arrow VIII of FIG. 6.
Figure 9A:
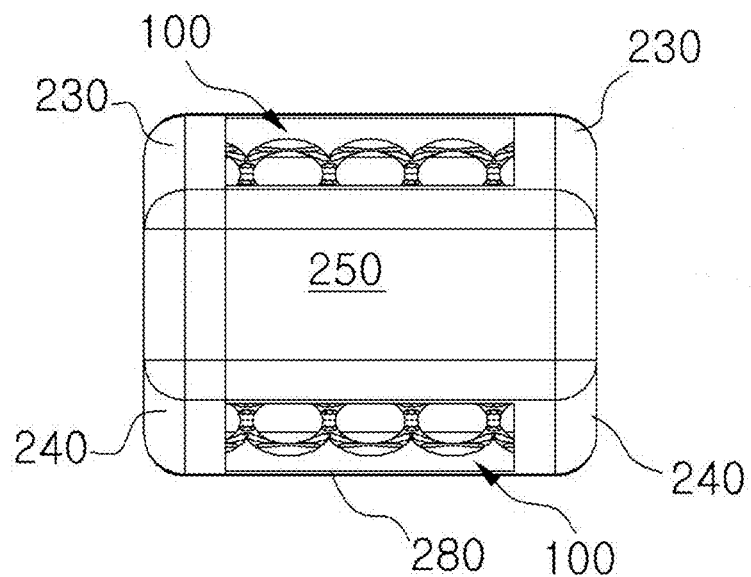
Figure 9B:
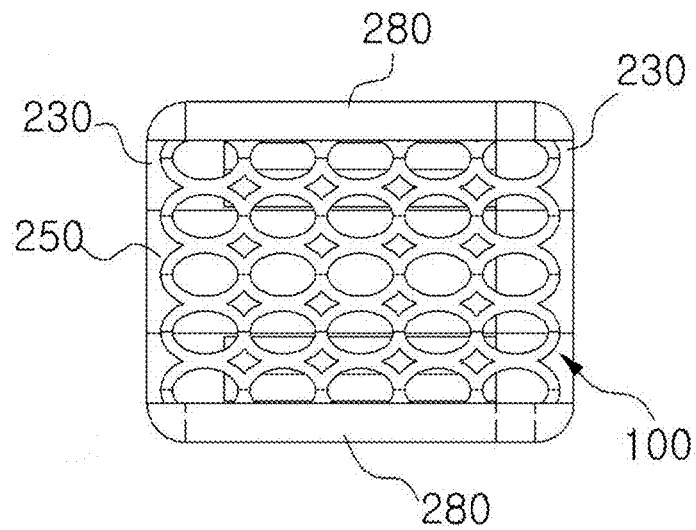

Also, FIG. 6 is a perspective view illustrating an outer appearance of a spinal implant having a unit structure that is printed by a 3D printer according to further another embodiment of the present invention, FIG. 7 is a conceptual plan view when viewed in a direction of an arrow VII of FIG. 6, FIG. 8 is a conceptual side view when viewed in a direction of an arrow VIII of FIG. 6, and FIGS. 9A and 9B are views when viewed in direction of arrows IXa and IXb of FIG. 6, wherein FIG. 9A is a conceptual front view, and FIG. 9B is a conceptual rear view.

Figure 10:
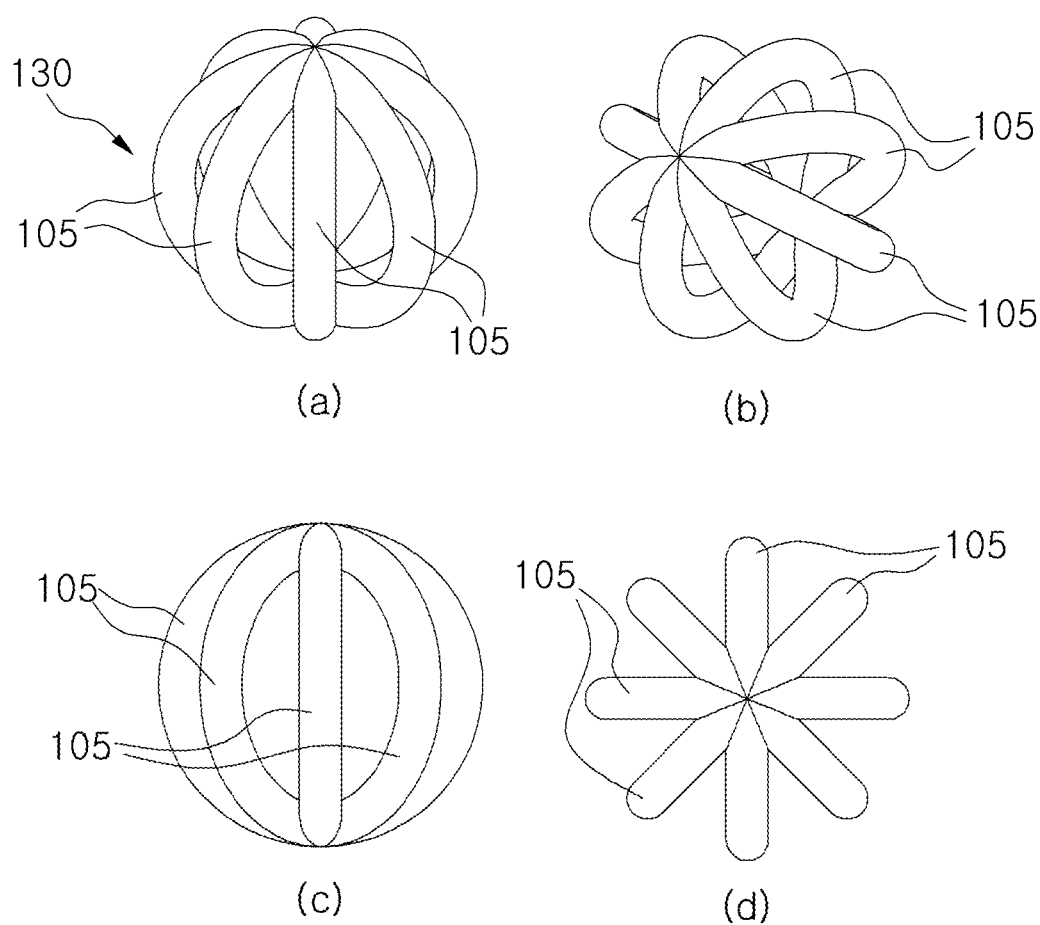
FIG. 10 is a conceptual view illustrating a structure of a third unit solid constituting a bone fusion unit that is a main part of a spinal implant having a unit structure that is printed by a 3D printer according to other embodiments of the present invention.
Figure 11:
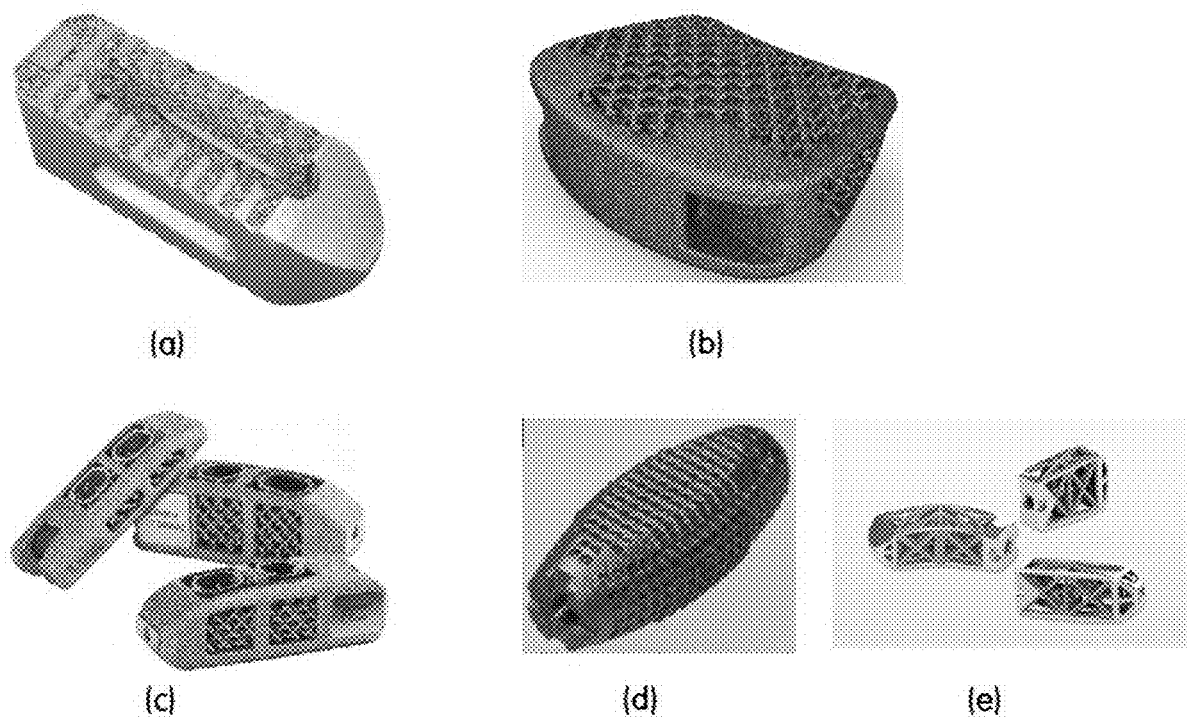
FIG. 11 is a photograph illustrating existing intervertebral fusion cages manufactured through a 3D printing manufacturing method.

Also, FIG. 10 is a conceptual view illustrating a structure of a third unit solid 130 constituting a bone fusion unit 100 that is a main part of a spinal implant having a unit structure that is printed by a 3D printer according to other embodiments of the present invention.

As illustrated in FIGS. 1A and 1B, the present invention may have a structure including the bone fusion unit 100 printed by using the 3D printer, which is inserted between vertebrae adjacent to each other and in which unit bodies constituted by at least one or more circular rings 105 are repeated with a certain pattern.

The foregoing embodiment as well as following various embodiments may be applied to the present invention.

First, the above-described certain pattern may have a structure including first and second layers 101 and 102 as illustrated in FIG. 1A.

In the first layer 101, a plurality of circular rings 105 are disposed on the same plane to form a row or column.

In the second layer 102, a plurality of circular rings 105 are disposed to form a row or column, which is perpendicular to that of the first layer 101.

Thus, in the above-described certain pattern, the pattern on which the first layer 101 and the second layer 102 coming into contact with each other are repeated upward, downward, left, right, forward, and backward. Thus, edges of the plurality of circular rings 105 come into contact with each other to form a porous bone fusion unit 100 on the whole.

In the above-described certain pattern, an embodiment of a structure including third and fourth layers 103 and 104 as illustrated in FIG. 1B may be applied.

First, in the third layer 103, a plurality of circular rings 105 are disposed on the same plane to form a row or column.

In the fourth layer 104, a plurality of circular rings 105 are disposed to form a row or column, which is perpendicular to that of the third layer 103.

Thus, the third layer 103 is disposed inclined at a predetermined angle with respect to a separate virtual plane (a plane through which a virtual line L passes in FIG. 1B). In the certain pattern, patterns on which the third layer 103 and the fourth layer 104 coming into contact with each other are repeated upward, downward, left, right, forward, and backward, and edges of the plurality of circular rings 105 come into contact with each other to form a porous bone fusion unit 100 on the whole.

As illustrated in FIGS. 2 to 5, the above-described certain pattern includes a first unit solid 100 in which at least two or more circular rings 105 cross each other to share a first virtual line l1 that passes through diameters of the circular rings 105 and thereby to form two intersections 111 and 112.

Here, in the above-described certain pattern, the plurality of first unit solids 110 are repeated upward, downward, left, right, forward, and backward, and the two intersections 111 and 112 respectively face a bottom surface of a vertebra 310 and a top surface a vertebra 320 adjacent to the vertebra 310.

Here, one intersection 112 of the two intersections 111 and 112 comes into contact with the other intersection 111 of the two intersections 111 and 112 of the first unit solid 110 adjacent to the first unit solid 110. Thus, the above-described first unit solid 110 forms the porous bone fusion unit 100 disposed in a lattice shape as illustrated in FIG. 3 on the whole.

As illustrated in FIGS. 6 to 9, in the above-described certain pattern, at least two or more circular rings 105 cross each other to share a second virtual line l2 that passes through diameters of the circular rings 105 to provide a structure including a second unit solid 120 that forms two intersections 121 and 122.

Here, in the above-described certain pattern, the second virtual line l2 passing through the two intersections 121 and 122 passes through a space between the vertebra 310 and the vertebra 320 adjacent to the vertebra 310, and the plurality of second unit solids 120 are repeated to come into contact with each other upward, downward, left, right, forward, and backward. Thus, the second unit solid 120 may form the porous bone fusion unit 100 in which a plurality of rows and columns are stacked in multi stages to repeatedly provide an 'X'-shaped structure when viewed from a side surface as illustrated in FIG. 8 on the whole.

That is, according to the present invention, as illustrated in FIGS. 1 to 9, the structure of the circular ring 105 that is the smallest unit for forming the bone fusion unit 100 may generate the elastic force for elastic deformation and elastic restoration with respect to the load and pressure applied in all directions between the vertebra 310 and the adjacent vertebra 320 to prevent the subsidence phenomenon from occurring between the vertebra 310 and the adjacent vertebra 320.

Particularly, the porous bone fusion unit 100 in which the 'X'-shaped structures are repeatedly stacked in the multi stages may adequately disperse and support the pressure and impact applied in all directions as well as the load applied downward between the vertebra 310 and the adjacent vertebra 320.

The present invention may further include a main frame 200 which is inserted between the vertebra 310 (hereinafter, referred to as a first vertebra 310) and the adjacent vertebra 320 (hereinafter, referred to as a second vertebra 320), provides an inner space for accommodating the bone fusion unit 100, and is printed together with the bone fusion unit 100 by using the 3D printer.

Here, as illustrated in the drawings, top and bottom surfaces, left and right surfaces, and a rear surface of the bone fusion unit 100 may be exposed to the outside so that a degree of the bone fusion increases between the first vertebra 310 and the second vertebra 320.

Here, referring again to FIG. 2, the main frame 200 may have a structure including a pair of upper bars 210 and 210, a pair of lower bars 220 and 220, upper insertion bars 230 and 230, and lower insertion bars 240 and 240.

The pair of upper bars 210 and 210 are members disposed in parallel to each other to face the bottom surface of the first vertebra 310, ad the pair of lower bars 220 and 220 are members disposed in parallel to each other to face the top surface of the second vertebra 320.

Also, the upper insertion bars 230 and 230 are members that respectively extend to be inclined downward from front ends of the pair of upper bars 210 and 210, and the lower insertion bars 240 and 240 are members that respectively extend to be inclined upward from front ends of the pair of lower bars 220 and 220.

Thus, as illustrated in the drawings, it is seen that the bone fusion unit 100 is disposed in an inner space that is defined by the pair of upper bars 210 and 210, the pair of lower bars 220 and 220, the upper insertion bars 230 and 230, and the lower insertion bars 240 and 240.

Also, the main frame 200 may further include a front finishing piece 250 having a flat plate shape, which is connected to a front end of each of the upper insertion bars 230 and 230 and the lower insertion bars 240 and 240.

Also, the main frame 200 may further include a first connection bar 260 that connects front ends of each of the upper insertion bars 230 and 230 and the lower insertion bars 240 and 240 to each other and comes into contact with an upper edge and a lower edge of the front finishing piece 250.

Also, the main frame 200 may further include a second connection bar 270 that connects front ends of each of the pair of upper bars 210 and 210 and the pair of lower bars 220 and 220 to each other and is disposed parallel to the first connection bar 260.

Also, the main frame 200 may further include a third connection bar 280 that connects rear ends of each of the pair of upper bars 210 and 210 and the pair of lower bars 220 and 220 to each other and is disposed parallel to the second connection bar 270.

Here, in some cases, when the main frame 200 has the structure according to the embodiment described with reference to FIGS. 6 to 9, which is more focused in more increasing a degree of the bone fusion and dispersing and supporting the load and the impact, the first connection bar 260 may be omitted.

Here, each of the bone fusion unit 100 and the main frame 200 may be made of titanium, a titanium alloy, or polyether ether ketone (PEEK), which is harmless to the human body, according to whether structural strength is priority, or the elasticity is priority.

As described above, the bone fusion unit 100 may be printed to provide the structure in which the two circular rings 105 are disposed to cross each other like the first and second unit solids 110 and 120. In addition, as illustrated in FIG. 10, the bone fusion unit 100 including the third unit solid 130 having a shape similar to a generally spherical shape by allowing two or more circular rings 105, for example, four circular rings 105 to cross each other may be printed together with the above-described main frame 200.

Particularly, in the case of the bone fusion unit 100 including the third unit solid 130, a more fine and dense porous structure than those of FIGS. 1 to 9 may be provided to induce fast bone fusion to the subject that suffers from degenerative spinal diseases.

Hereinafter, the operations and effects according to the present invention will be described as follows.

First, the present invention may include the bone fusion unit printed by using the 3D printer, which is inserted between the vertebra 310 and the adjacent vertebra 320 in which the unit bodies constituted by at least one or more circular rings 105 are repeated with the certain pattern. Thus, the subsidence phenomenon may be prevented from occurring through the unit body having the form of the circular ring 105 that is capable of generating the elastic force between the vertebra 310 and the vertebra 320 while significantly improving the bone fusion, thereby obtaining superior procedure results.

Particularly, the present invention may provide the bone fusion unit 100 having the porous structure on the whole by using the certain pattern of the unit bodies including the circular rings 105 to provide the most similar tissue structure to the existing vertebrae and faithfully perform the natural function of the intervertebral fusion cage through the elastic structure similar to the existing bone tissue even through the long time elapses.

Also, according to the present invention, the spinal implant including the bone fusion unit 100 may be manufactured through the printing using the 3D printer. Thus, if a more complicated and fine structure is accurately designed by the 3D graphic tool, the firm structure that exhibits the porous elastic force most similar to that of the bone tissue of the subject may be provided through the simple printing.

Furthermore, the main frame 200 may be integrally printed together by using the 3D printer to maintain the durability with respect to the load, the pressure, and the impact between the vertebrae together with the bone fusion unit 100. In some cases, the entire spinal implant may be made freely selectable from a variety of harmless materials such as titanium, a titanium alloy or polyether ether ketone (PEEK).

Here, according to the present invention, when the spinal implant is entirely made of titanium or a titanium alloy, since it does not slip so well due to the high surface friction, the firm seating state that is not separated between the vertebra 310 and the adjacent vertebra 320 may be maintained.

Here, when the spinal implant according to the present invention is made of the above-described PEEK, since the spinal implant having the superior elastic modulus is provided to the subject, even though the long time elapses after the procedure to complete the bone fusion or while the bone fusion is performed after the procedure, the subsidence of the facing surfaces of the vertebra 310 and the adjacent vertebra 320 may be securely prevented.

As described above, the present invention may provide the spinal implant having the unit structure printed by using the 3D printer to generate the elastic force like the existing vertebrae while the bone fusion is performed, thereby obtaining the superior procedure results.

According to the present invention having the above-described constitutions, the following effects may be attained.

First, the present invention may include the bone fusion unit printed by using the 3D printer, which is inserted between the vertebrae adjacent to each other and in which the unit bodies constituted by at least one or more circular rings are repeated with the certain pattern. Thus, the subsidence phenomenon may be prevented from occurring while the bone fusion is performed as well as after the bone fusion is completed after the procedure through the unit body having the circular ring shape that is capable of generating the elastic force between the vertebrae adjacent to each other while significantly improving the bone fusion, thereby obtaining superior procedure results.

Particularly, the present invention may provide the bone fusion unit having the porous structure on the whole by using the certain pattern of the unit bodies including the circular rings to provide the most similar tissue structure to the existing vertebrae and faithfully perform the natural function of the intervertebral fusion cage through the elastic structure similar to the existing bone tissue even through the long time elapses.

Also, according to the present invention, the spinal implant including the bone fusion unit may be manufactured through the printing using the 3D printer. Thus, if a more complicated and fine structure is accurately designed by the 3D graphic tool, the firm structure that exhibits the porous elastic force most similar to that of the bone tissue of the subject may be provided through the simple printing.

Furthermore, the main frame may be integrally printed together by using the 3D printer to maintain the durability with respect to the load, the pressure, and the impact between the vertebrae together with the bone fusion unit. In some cases, the entire spinal implant may be made freely selectable from a variety of harmless materials such as titanium, a titanium alloy or polyether ether ketone (PEEK).

Here, according to the present invention, when the spinal implant is entirely made of titanium or a titanium alloy, since it does not slip so well due to the high surface friction, the firm seating state that is not separated between the vertebrae adjacent to each other may be maintained.

Here, when the spinal implant according to the present invention is made of the above-described PEEK, since the spinal implant having the superior elastic modulus is provided to the subject, even though the long time elapses after the procedure, the subsidence of the facing surfaces of the vertebrae adjacent to each other may be securely prevented.

Also, it should be understood that numerous other modifications and embodiments can be devised by those skilled in the art that will fall within the scope of the fundamental technical idea of the principles of the present invention.

What is claimed is:

1. A spinal implant having a unit structure printed by using a 3D printer, the spinal implant comprising a bone fusion unit printed by using the 3D printer, configured to be inserted between a first vertebra and a second vertebra that is adjacent to the first vertebra, and constituted by a plurality of unit structures repeated in a lattice pattern,
   wherein each of the plurality of unit structures comprises at least two or more circular rings crossing each other to share a virtual line that passes through a diameter of the at least two or more circular rings and thereby to provide a first intersection and a second intersection,
   wherein the first and second intersections face a bottom surface of the first vertebra and a top surface of the second vertebra, respectively, when the spinal implant is inserted between the first and second vertebrae, and
   wherein, in the lattice pattern, the plurality of unit structures are repeated upward, downward, left, right, forward, and backward in a same orientation.

2. The spinal implant of claim 1, wherein the lattice pattern comprises:
   a first layer having a first plurality of circular rings disposed on a same plane to provide a row or a column; and
   a second layer disposed to be perpendicular to the first layer and having a second plurality of circular rings,
   wherein, in the lattice pattern, a perpendicular pattern formed by the first layer and the second layer coming into contact with each other is repeated upward, downward, left, right, forward, and backward, and
   edges of the plurality of circular rings come into contact with each other.

3. The spinal implant of claim 1, further comprising a main frame configured to be inserted between the first vertebra and the second vertebra, provides an inner space for accommodating the bone fusion unit, and is printed together with the bone fusion unit by using the 3D printer,
   wherein top and bottom surfaces, left and right surfaces, and a rear surface of the bone fusion unit are exposed to the environment of the first and second vertebrae when the spinal implant is inserted between the first and second vertebrae.

4. The spinal implant of claim 3, wherein the main frame comprises:
   a pair of upper bars disposed in parallel to each other to face a bottom surface of the first vertebra when the spinal implant is inserted between the first and second vertebrae;
   a pair of lower bars disposed in parallel to each other to face a top surface of the second vertebra when the spinal implant is inserted between the first and second vertebrae;
   a pair of upper insertion bars extending to be inclined downward from a front end of each of the pair of upper bars; and
   a pair of lower insertion bars extending to be inclined upward from a front end of each of the pair of lower bars,
   wherein the bone fusion unit is disposed in an inner space that is defined by the pair of upper bars, the pair of lower bars, the pair of upper insertion bars, and the pair of lower insertion bars.

5. A spinal implant having a unit structure printed by using a 3D printer, the spinal implant comprising a bone fusion unit printed by using the 3D printer, configured to be inserted between a first vertebra and a second vertebra that is adjacent to the first vertebra, and constituted by a plurality of unit structures repeated in a lattice pattern,
   wherein each of the plurality of unit structures comprises at least two or more circular rings crossing each other to share a virtual line that passes through a diameter of the at least two or more circular rings and thereby to provide a first intersection and a second intersection,
   wherein, in the lattice pattern, the plurality of unit structures are repeated upward, downward, left, right, forward, and backward in a same orientation, and
   the virtual line passing through the first and second intersections passes through a space between the first vertebra and the second vertebra when the spinal implant is inserted between the first and second vertebrae.

6. The spinal implant of claim 5, wherein the lattice pattern comprises:
   a first layer having a first plurality of circular rings disposed on a same plane to provide a row or a column; and
   a second layer disposed to be perpendicular to the first layer and having a second plurality of circular rings,
   wherein the first layer is disposed to be inclined at a predetermined angle with respect to a separate virtual horizontal plane of the bone fusion unit,
   in the lattice pattern, a perpendicular pattern formed by the first layer and the second layer coming into contact with each other is repeated upward, downward, left, right, forward, and backward, and
   edges of the plurality of circular rings come into contact with each other.

7. The spinal implant of claim 5, further comprising a main frame configured to be inserted between the first vertebra and the second vertebra, provides an inner space for accommodating the bone fusion unit, and is printed together with the bone fusion unit by using the 3D printer,
   wherein top and bottom surfaces, left and right surfaces, and a rear surface of the bone fusion unit are exposed to the environment of the first and second vertebrae when the spinal implant is inserted between the first and second vertebrae.

8. The spinal implant of claim 7, wherein the main frame comprises:
   a pair of upper bars disposed in parallel to each other to face a bottom surface of the first vertebra when the spinal implant is inserted between the first and second vertebrae;
   a pair of lower bars disposed in parallel to each other to face a top surface of the second vertebra when the spinal implant is inserted between the first and second vertebrae;
   a pair of upper insertion bars extending to be inclined downward from a front end of each of the pair of upper bars; and a pair of lower insertion bars extending to be inclined upward from a front end of each of the pair of lower bars,
wherein the bone fusion unit is disposed in an inner space that is defined by the pair of upper bars, the pair of lower bars, the pair of upper insertion bars, and the pair of lower insertion bars.

\* \* \* \* \*